United States Patent [19]
Jones et al.

[11] Patent Number: 5,939,569
[45] Date of Patent: Aug. 17, 1999

[54] EPOXIDATION PROCESS

[76] Inventors: C. Andrew Jones, 912 Pritchard Pl., Newtown Square, Pa. 19073; Roger A. Grey, 111 Piedmont Rd., West Chester, Pa. 19382

[21] Appl. No.: 09/037,399

[22] Filed: Mar. 10, 1998

[51] Int. Cl.⁶ .................................................. C07D 303/00
[52] U.S. Cl. ............................................................ 549/512
[58] Field of Search ................................................. 549/512

Primary Examiner—Amelia Owens

[57] ABSTRACT

A process for converting an olefin such as propylene to the corresponding epoxide is described wherein the olefin, hydrogen and oxygen are contacted with a catalyst comprised of gold on a zirconium-containing support such as zirconia.

11 Claims, No Drawings

EPOXIDATION PROCESS

FIELD OF THE INVENTION

This invention relates to a method for converting an olefin to the corresponding epoxide by oxidation of the olefin with oxygen in the presence of hydrogen using a catalyst comprised of gold on a support comprised of zirconium.

BACKGROUND OF THE INVENTION

The direct oxidation of ethylene to ethylene oxide is practiced commercially using supported silver catalysts. Unfortunately, the analogous direct oxidation of olefins containing allylic hydrogens such as propylene generally exhibits significantly lower selectivity to the epoxide due to side reactions. In view of the problems encountered with supported silver catalysts of the type used for ethylene oxidation, alternative catalyst systems have been explored for use with higher olefins in recent years.

For example, U.S. Pat. No. 5,623,090 describes the production of an epoxide from an unsaturated hydrocarbon by passing a mixture comprised of molecular hydrogen, the unsaturated hydrocarbon and oxygen through a bed of a catalyst comprising a titanium dioxide carrier and ultrafine gold particles deposited on the carrier. According to the patent, "it is essential to use gold and titanium dioxide in combination." The inventors named in the patent have similarly reported (Hayashi et al., Symposium on Heterogeneous Hydrocarbon Oxidation, Presented before the Division of Petroleum Chemistry, Inc., 211th National Meeting, American Chemical Society, New Orleans, La, Mar. 24–29, 1996) that the use of gold supported on metal oxides other than $TiO_2$ does not lead to the partial oxidation of propylene. Other publications related to supported gold catalysts have also emphasized the criticality of having titanium present in the support in order to attain an active olefin epoxidation catalyst. See, for example, WO 97/34692, WO 98/00413, WO 98/00414, and WO/00415.

SUMMARY OF THE INVENTION

The present invention provides a process for preparing an epoxide comprising contacting an olefin with oxygen in the presence of hydrogen and a catalyst comprising gold on a support, wherein the support is comprised of zirconium. The finding that gold on a zirconium-containing support, which can be free or essentially free of titanium, is capable of selectively converting an olefin to the corresponding epoxide was quite surprising in view of the general belief in the prior art that no epoxidation activity could be obtained unless titanium is present in the support.

DETAILED DESCRIPTION OF THE INVENTION

Although any olefin can be employed in the process of this invention, the process is particularly well-suited for the epoxidation of relatively light ethylenically unsaturated compounds containing allylic hydrogens. Monoolefins are preferred, although compounds such as dienes which contain two or more carbon-carbon double bonds could also be utilized. The olefin can be a hydrocarbon containing only carbon and hydrogen atoms, but can also be substituted with one or more halide, ether, ester or alcohol moieties or the like. The use of $C_3$–$C_6$ olefins is particularly preferred, especially where the process is to be carried out in the vapor phase. Non-limiting examples, of suitable olefins include ethylene, propylene, 1-butene, 2-butene, isobutylene, 1-pentene, 2-pentene, butadiene, allyl alcohol, allyl chloride, styrene, cyclohexene and the like. Most preferably, the olefin is propylene.

The amount of olefin used in the process can be varied over a wide range and is not considered to be particularly critical. The optimum quantity of olefin will depend upon a number of process variables such as the reactor design, the relative amounts of hydrogen, oxygen, and optional diluent employed, reaction temperature, and so forth, but may be easily ascertained by routine experimentation. In general, it will be desirable to operate the process so that the olefin is in molar excess relative to the oxygen in order to improve epoxide productivity. Typical olefin concentrations will be from about 5 to 85 mole percent based on the total moles of olefin, oxygen, hydrogen and optional diluent.

The oxygen which is required in the process can be from any suitable source such as air or essentially pure molecular oxygen. Other compounds which are capable of functioning as sources of oxygen such as ozone and nitrogen oxides could also be employed, although for economic reasons molecular oxygen is preferred. Provided there is at least sufficient oxygen present to produce the desired epoxide, the quantity of oxygen can be varied over a wide range with the optimum concentration being readily determinable by routine experimentation. As stated previously, it will ordinarily be desirable to operate the process using an olefin to oxygen molar ratio of greater than 1. Selectivity to the desired epoxide may thereby be enhanced due to a reduced tendency to form combustion or over-oxidation products such as carbon dioxide. Typically, the quantity of oxygen is between 1 and 25 mole percent based on the total moles of olefin, hydrogen, oxygen and optional diluent.

The hydrogen required for use in the process may be supplied from any suitable source, including, for example, molecular hydrogen obtained by alkane or alcohol dehydrogenation. Such dehydrogenation may be carried out in the epoxidation reactor itself so as to form the necessary hydrogen in situ. The hydrogen is used in an amount effective to convert the olefin to the corresponding epoxide, with the hydrogen concentration typically being in the range of 0.1 to 30 mole percent based on the total moles of olefin, hydrogen, oxygen and optional diluent.

Although the presence of a diluent is optional, it has been found to be helpful as a means of removing and dissipating the heat generated during the process. In a vapor phase process, the diluent may also be utilized to render the olefin/oxygen/hydrogen mixture non-flammable. Any gas or liquid which does not interfere with the desired epoxidation reaction may be utilized, preferably one that is essentially inert (non-reactive) under the epoxidation conditions. Suitable gaseous diluents, which are preferably used when the reactants are in the vapor phase when contacted with the catalyst, include helium, nitrogen, argon, methane, ethane, propane, steam, carbon dioxide and the like and mixtures thereof. Where the reactants are contacted in the liquid phase with the catalyst, then the diluent may be any compound which is liquid under the temperature and pressure conditions employed. Preferably, the diluent liquid is resistant to oxidation and is thermally stable. Example of suitable liquid diluents include water as well as organic solvents such as halogenated aliphatic and aromatic compounds.

The amount of diluent, if any, is preferably less than about 80 mole percent based on the total number of moles of olefin, oxygen, hydrogen and diluent.

The catalyst utilized in the process of the invention is comprised of gold and a zirconium-containing support. As explained earlier the catalyst need not contain any titanium (i.e., the catalyst can be essentially free of titanium). While the particle size of the gold is not believed to be particularly critical, typically the average gold particle size will be in the range of 1 to 100 nm. The gold can exist in discrete particles consisting essentially of gold or alternatively in discrete particles comprised of gold and one or more other elements. The gold can exist in the zero valent (metallic) state or in a positive valence state or in some combination of different valence states.

The zirconium contained in the support may be in a variety of forms, but preferably is in a positive oxidation state (most preferably, an oxidation state of +3 and/or +4). Amorphous as well as crystalline oxides of zirconium may be utilized as the support. Zirconium dioxide (zirconia), for example, may be used in any of its four different crystalline phases (monoclinic, tetragonal, orthorhombic, or cubic fluorite). The naturally occurring mineral baddeleyite may be suitably used as a source of zirconium oxide.

Zirconates can also be suitably employed as the catalyst support. The zirconate may be either crystalline or amorphous. If so desired, zirconates of the promoter elements to be discussed hereinafter in more detail may be utilized such as the zirconates of alkali metals, alkaline earth metals, lanthanide metals, and actinide metals. Specific illustrative examples of suitable zirconates include magnesium zirconate, calcium zirconate, barium zirconate, strontium zirconate, sodium zirconate, and potassium zirconate.

Crystalline and amorphous zirconosilicates, particularly those having a porous structure, also are suitable for use as the support. Non-limiting examples of porous zirconosilicates include porous amorphous zirconosilicates, porous layered zirconosilicates, and crystalline porous zirconosilicates, particularly those having zeolitic or molecular sieve structures where zirconium atoms are substituted for silicon atoms in the framework. Microporous and mesoporous crystalline zirconosilicates can be utilized, including but not limited to those materials having framework structures isomorphous with ZSM-5, ZSM-11, zeolite beta, ZSM-12, ZSM48 and MCM-41.

Illustrative publications disclosing zirconosilicates of different types capable of being used as supports in the present process include U.S. Pat. Nos. 5,399,336, 5,246,688, 5,108,579, 5,374,411, 5,015,453, 4,576,805, 3,329,480, 3,329,481, and 3,329,482, European Patent Publication Nos. 466,545 and 796,821, Tuel et al., "Zirconium Containing Mesoporous Silicas: New Catalysts for Oxidation Reactions in the Liquid Phase," *Chem. Commun.* 651–652 (1996), Wang et al., *Stud. Surf. Sci Catal.* 83, 67–74 (1994), Dongare et al., *Zeolites* 11, 690 (1991), each of which is incorporated herein by reference in its entirety.

Another suitable support for the catalyst used in the process of this invention comprises zirconium dispersed on silica or other siliceous substance. The zirconium may be dispersed over the silica surface in either a disorganized (amorphous) or organized (crystalline) phase, or some combination thereof. Any type of silica or other siliceous substance can be used in the support provided that it permits an active catalyst composition to be obtained. Amorphous as well as crystalline silica are suitable for use including, for example, fumed silica, silica gel, precipitated silica, precipitated silica gels, silicalite and mixtures thereof. The zirconium loading on the silica is typically in the range of from about 0.05 to 20 weight percent based on the weight of the silica. Methods of depositing zirconium on silica include, for example, impregnation of the silica support using a solution of a zirconium compound such as a zirconium alkoxide, zirconium sulfate, zirconium halide, or zirconium carboxylate, drying, and optionally calcining. Adsorption of a zirconium compound onto the silica may also be practiced, as can solvolysis of zirconium alkoxides in the presence of silica. The zirconium may also be deposited on the silica using gas phase techniques such as exposing the silica to a gas stream comprised of a volatile zirconium compound such as a zirconium halide or zirconium alkoxide, preferably at an elevated temperature.

Another type of support suitable for use in the present invention comprises zirconium dispersed on a silicate of a promoter element. The silicate may be amorphous or crystalline and may, for example, be a silicate of an alkali metal, alkaline earth metal, lanthanide rare earth metal, or actinide metal such as magnesium silicate, calcium silicate, barium silicate, and the like.

The gold loading on the zirconium-containing support must be sufficiently high so as to impart the desired level of catalyst activity to the catalyst, as in the absence of gold no significant conversion of olefin to the corresponding epoxide is observed under the reaction conditions of this process. The optimum amount of gold will vary depending upon the other reaction parameters selected, but levels of from about 0.01 to 20 weight percent gold based on the total weight of support have been found to be effective.

The gold can be deposited on the zirconium-containing support by any of the techniques known in the art for placing a metal on a solid support including for example, impregnation, co-precipitation, chemical vapor deposition, ion-exchange, and deposition by precipitation.

Methods developed for depositing gold on other metal oxides such as titanium dioxide may be readily adapted for use with the zirconium-containing supports utilized in this invention. Such methods are described in detail in the following publications, each of which is incorporated herein by reference in its entirety: WO 98/00413; WO 98/00414; WO 98/00415; WO 97/34692; Haruta et al, *J. Catal.*, 115, pp. 301–309 (1989); Tsubota et al. in "Preparation of Catalysts V", *Stud. Surf. Sci. Catal.*, 63, G. Poncelet et al., eds, Elsevier, pp. 695–704 (1991); Kobayashi et al., *Sensors and Actuators*. B1, pp. 222–225 (1990); U.S. Pat. No. 5,623,090; Haruta et al., *J. Catal.*, 144,175 (1993); U.S. Pat. No. 4,839,327; U.S. Pat. No. 4,937,219; U.S. Pat. No. 5,051,394; Tsubota et al. in "Preparation of Catalysts VI", G. Poncelet et al. eds., Elsevier, pp. 227–235 (1995); Okumura et al., *Solid State Ionics*, 95,143 (1997); U.S. Pat. No. 4,698,324.

One suitable method for preparing a catalyst suitable for use in the present epoxidation process involves the deposition and precipitation of gold in the form of a hydroxide onto the surface of the zirconium-containing support. For example, an aqueous solution of a water soluble gold hydroxide compound (obtained, for instance, by adjusting the pH of an aqueous solution of an acidic gold compound to the neutral or slightly basic range with a base such as alkali metal hydroxide) may be combined with a zirconium-containing support such as zirconia to obtain a suspension of the support having the gold hydroxide compound immobilized thereon. The support is then separated from the suspension by filtration, decantation, centrifugation or other such means, optionally washed with one or more portions of a suitable washing solvent such as water, and then dried and/or calcined (for example, by heating in air or under an inert gas atmosphere at a temperature greater than 300° C.).

One or more promoters may be incorporated into the catalyst in order to improve its performance. Promoters which enhance the productivity of the catalyst by increasing catalyst activity or selectivity to epoxide or extending the useful life of the catalysts are particularly advantageous. Preferably, the promoter may be an alkali metal selected from Group I of the Periodic Table such as lithium, sodium, potassium, rubidium or cesium or an alkaline earth metal selected from Group II of the Periodic Table such as beryllium, magnesium, calcium, strontium or barium. The lanthanide rare earth metals and/or actinide metals may also be utilized as promoters. Typically, the amount of promoter deposited on the zirconium-containing support will be between about 0.1 and 10 weight percent based on the total weight of the catalyst. Where the support material is comprised of a zirconate or silicate of the promoter, the promoter levels may, of course, be considerably greater then 10 weight percent.

Optionally, the catalyst of this invention can be extruded with, bound to, or supported on a second support having a chemical composition different from that of the zirconium-containing support. The second support may be utilized in order to improve some characteristic of the catalyst such as, for instance, its physical properties (strength or attrition resistance) or as a binder to hold together catalyst particles. Example of materials usable as second supports include silica, alumina, titania, aluminasilicates, clays, magnesia, carbon and the like and mixtures thereof. The final catalyst may be formed into any of the shapes conventionally employed in the heterogenous catalyst art, including, for example, powders, pellets, spheres, monoliths, granules, extrudates and the like.

The process of the invention can be carried out in a reactor of any conventional design suitable for vapor phase or liquid phase processes including, for example, batch, fixed bed, transport bed, fluidized bed, moving bed, shell tube, bubble column and trickle bed reactors. The reactor may be operated with continuous, intermittent, or swing flow. As the process is exothermic, suitable means should be provided for removing or otherwise controlling the heat generated so that catalyst activity and selectivity may be optimized.

It will generally be desirable to contact the reactants with the catalyst at a temperature in the range of from about 20° C. to 250° C., with the optimum temperature for the particular catalyst, olefin, reactant ratios and other process variables selected being readily ascertainable by routine experimentation. The pressure may typically range from about atmospheric up to about 5000 psig. Where the process is practiced in the vapor phase, the space velocity of the feed gas (olefin, hydrogen, oxygen, optional diluent(s)) though the reactor will generally be in the range of from 100 to 10,000 $hr^{-1}$ mL/g catalyst.

Although the catalyst composition and reaction conditions may be selected so as to permit the process to be operated at a satisfactorily high level of productivity over an extended period of time, the catalyst may eventually decline in activity and/or epoxide selectivity, such that continued operation is no longer economically attractive. The catalyst may be either replaced or regenerated at such point. Suitable regeneration procedures include, for example, heating the spent catalyst at an elevated temperature (e.g. 150° C. to 500° C.) in a gas stream containing hydrogen and/or oxygen (an inert gas or water may also be present; preferably, the regeneration is performed in the absence of olefin or other reactive species).

EXAMPLES

Example 1

A catalyst is prepared by the following deposition-precipitation procedure. Chloroauric acid (0.252g) was dissolved in 400 mL deionized water. After increasing the temperature of the resulting solution to 70° C., the pH of the solution was adjusted to 7.5 by adding 5% aqueous sodium hydroxide. Zirconia (10 g) was then added to the solution and the resulting suspension stirred for 1 hour. The solids were separated from the aqueous solution by filtration, washed with 1 L deionized water, and filtered again. This washing and filtering sequence was repeated twice more. The washed solids thereby obtained were vacuum-dried at room temperature for 16 hours, dried in air at 100° C. for 4 hours, and finally calcined in air four hours at 400° C. The catalyst thereby obtained had a composition by elemental analysis corresponding to 1.0 wt % Au, 0.02 wt % Ti, 0.03 wt % Na, and 0.01 wt % Cl. The surface area of the catalyst was 43.6 $m^2/g$.

A 1.6 g (2 mL) sample of the aforedescribed catalyst was loaded into a tubular reactor. A number of different runs (A-G) were then performed wherein a feed stream containing hydrogen, oxygen, propylene, and nitrogen was passed through the catalyst bed and the gaseous products exiting the reactor analyzed by gas chromatography. The catalyst was also analyzed at the end of each run to determine the quantity of nonvolatile solids accumulated on the catalyst during the run. This was accomplished by purging with nitrogen and then passing a mixture of 2.5% oxygen in nitrogen through the catalyst for approximately 4 hours at 400° C. The effluent from the reactor was collected and then analyzed by gas chromatography to determine the carbon dioxide concentration. The carbon content of the catalyst was then calculated from the $CO_2$ measurement based on the assumption that all of the carbon had been converted to $CO_2$ during catalyst regeneration. The effects of varying the feedstream composition, temperature and pressure are shown in Table I.

TABLE I

| Run | A | B | C | D | E | F | G |
|---|---|---|---|---|---|---|---|
| Temp. (° C.) | 50 | 37 | 50 | 40 | 40 | 40 | 40 |
| Pressure (psig) | 15 | 15 | 15 | 50 | 85 | 85 | 85 |
| Feed stream | | | | | | | |
| $H_2$,% | 9 | 9 | 8 | 9 | 9 | 14 | 11 |
| $O_2$, % | 4.2 | 4.1 | 4.2 | 4.2 | 4.3 | 3.6 | 3.4 |
| $C_3H_6$, % | 8 | 9 | 9 | 9 | 8 | 15 | 21 |
| GHSV($hr^{-1}$) | 1320 | 1320 | 660 | 1320 | 1320 | 780 | 1620 |
| Run Time(hr) | 15 | 4 | 5 | 15 | 3 | 15 | 17 |
| Cumulative Results | | | | | | | |
| $C_3H_6$ Conv. (%) | 0.4 | 0.6 | 1.2 | 0.4 | 1.3 | 0.4 | 0.2 |
| Selectivity (%) | | | | | | | |
| Propylene Oxide | 8 | 6 | 6 | 20 | 11 | 27 | 30 |
| Propane | 0 | 3 | 6 | 5 | 3 | 5 | 11 |
| $CO_2$ | 7 | 5 | 9 | 4 | 4 | 2 | 2 |
| Acetone | 3 | 3 | 4 | 10 | 6 | 22 | 15 |
| Non-volatile solids | 82 | 83 | 75 | 61 | 76 | 44 | 42 |
| Gas Phase Distribution (mole %) | | | | | | | |
| Propylene Oxide | 44 | 35 | 24 | 51 | 46 | 48 | 52 |
| Propane | 0 | 18 | 24 | 13 | 13 | 9 | 19 |
| $CO_2$ | 39 | 29 | 36 | 10 | 17 | 4 | 3 |
| Acetone | 17 | 18 | 16 | 26 | 25 | 39 | 26 |

We claim:

1. A process of preparing an epoxide comprising contacting an olefin with oxygen in the presence of hydrogen and a catalyst comprising gold on a support, wherein the support is comprised of zirconium and is essentially free of titanium.

2. The process of claim 1 wherein the olefin is a $C_3$–$C_6$ olefin.

3. The process of claim 1 wherein the support is comprised of an oxide of zirconium.

4. The process of claim 1 wherein the catalyst is comprised of 0.05 to 5.0 weight percent gold.

5. The process of claim 1 wherein said contacting is performed at a temperature of from 20° C. to 250° C.

6. The process of claim 1 wherein the support is comprised of zirconium dispersed on silica.

7. The process of claim 1 wherein the support is comprised of a zirconosilicate.

8. The process of claim 1 wherein said contacting is performed in a vapor phase.

9. The process of claim 1 wherein said contacting is performed in a liquid phase.

10. The process of claim 1 wherein the catalyst is additionally comprised of a promotor selected from the group consisting of alkali metals, alkaline earth metals, lanthamide rare earth metals, actinide metals and combinations thereof.

11. The process of claim 1 wherein a diluent is additionally present during said contacting.

\* \* \* \* \*